United States Patent
Jaunakais et al.

(10) Patent No.: US 6,696,300 B1
(45) Date of Patent: Feb. 24, 2004

(54) ARSENIC ANALYSIS

(75) Inventors: Ivars Jaunakais, Rock Hill, SC (US); Lea Marianne Jaunakais, Rock Hill, SC (US); Corlyss Brown Lewis, Rock Hill, SC (US)

(73) Assignee: Industrial Test Systems, Inc., Rock Hill, SC (US)

( * ) Notice: Subject to any disclaimer, the term of this patent is extended or adjusted under 35 U.S.C. 154(b) by 278 days.

(21) Appl. No.: 10/045,387

(22) Filed: Nov. 9, 2001

(51) Int. Cl.$^7$ ................................................ G01N 33/20

(52) U.S. Cl. ........................ 436/73; 436/177; 436/175

(58) Field of Search ................................ 436/73–75, 177; 210/752, 759, 902; 423/87

(56) References Cited

U.S. PATENT DOCUMENTS 5,330,560 A * 7/1994 Chao et al. ..................... 95/95
2002/0000414 A1   1/2002 Kroll

FOREIGN PATENT DOCUMENTS

SU          715508       * 2/1980

OTHER PUBLICATIONS

McCleskey et al. Cation–exchange separation of interfering metals from acid mine waters for accurate determination of total arseing and arsenic (III) by hydride generation–atomic absorption spectrometry: http://wwwbrr.cr.usgs.gov/Arsenic/FinalAbsPDF/mcc.*
Trung et al. "Preconcentration of arsenic species in environmental waters by solid phase extraction using metal–loaded chelatin resins", Analytical Sciences 2001, v. 17, Suppl. i1219–i1223.*
Tan et al. "Determination of As(V) and As(III) in ferric sulfate–sulfuric acid leaching media by ion chromatography", Anal. Chem 1985, 57, pp. 2615–2620.*
Hach Company Arsenic Test Kit Information & Test Procedure (2000) Merck Arsenic Test Information & Procedure.
PurTest® Arsenic Information and Procedure (2000).
Hironaka Dec. 1998 (AAN) Test Kit Information & Procedure.
Merck Index, Tenth Edition (1983), p. 1455.

* cited by examiner

*Primary Examiner*—Jill Warden
*Assistant Examiner*—Yelena Gakh
(74) *Attorney, Agent, or Firm*—Timothy R. Kroboth

(57) ABSTRACT

An improved method for the analysis of arsenic in an aqueous sample, is disclosed. In accordance with the inventive method, arsenic is reduced to arsine gas in an acidic aqueous reaction environment and in the presence of an effective amount of an agent for increasing the rate of arsine gas production. Beneficially, metal cations are used as rate-increasing agents.

20 Claims, No Drawings

ARSENIC ANALYSIS

FIELD OF THE INVENTION

This invention relates to analysis of the level of arsenic in an aqueous sample.

BACKGROUND OF THE INVENTION

Controversy currently exists over what level of arsenic in drinking water is acceptable. But there is no controversy that there is a need to be able to determine the arsenic level in natural waters, drinking water and groundwater. Also beneficial is being able to determine the arsenic level in humans, soil, pharmaceuticals, prepared biological materials and foods, and to monitor the arsenic level in certain industrial processes.

Commercially available tests for the analysis of arsenic are exemplified by tests of Merck and Hach, and work by the reduction of arsenic, in particular inorganic arsenic compounds such as trivalent and pentavalent arsenic compounds, in an acidic aqueous environment to arsine gas. According to the Hach test description, hydrogen gas is also generated. Thus, using zinc in the arsenic reduction reaction, reduction to arsine gas may include the following reactions:

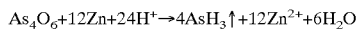

$$As_4O_6 + 12Zn + 24H^+ \rightarrow 4AsH_3\uparrow + 12Zn^{2+} + 6H_2O$$

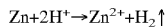

$$Zn + 2H^+ \rightarrow Zn^{2+} + H_2\uparrow$$

In these analyses, a closed reaction bottle providing a headspace above the aqueous reaction mixture, is used for the arsenic reduction reaction, and the bottle cap holds a mercuric bromide test strip in the headspace. In this way, mercuric bromide indicator is appropriately located for reaction with arsine gas, yet spaced away from the aqueous mixture to reduce contact by the aqueous mixture. These analyses instruct that after a reaction time of 30 minutes, the indicator on the test strip may be visually evaluated for any change from white to yellow to brown.

In the Merck analysis, liquid hydrochloric acid is used for sample acidification, and acidification is carried out after zinc powder is added to the aqueous sample. An evaluation of pH after the acidification but without the zinc powder addition, indicates that the acidification adjusts pH to less than 0.8.

In the Hach analysis, a 50 ml aqueous sample is adjusted to a pH of about 9, and then Oxone® is added to the alkaline sample to oxidize hydrogen sulfide to sulfate ion to prevent interference with the analysis. Thereafter, according to test details, EDTA salts, which are typically used as a chelating agent, are added. Then, the sample is acidified using sulfamic acid powder, to a pH of about 1. Then, reduction of arsenic to arsine gas is carried out, during which the reaction mixture is swirled twice. A reactive pad impregnated with mercuric bromide, reacts with the arsine gas. To quantify both organic and inorganic arsenic, a liquid sample is subjected to a boiling water bath for 30 minutes after the pH adjustment and Oxone® addition.

Despite advances in the analysis of arsenic, there remains a significant need for an improved arsenic test.

SUMMARY OF THE IMVENTION

In accordance with the present invention, an improved method for the analysis of arsenic is provided. In the improved method, arsenic is reduced to arsine gas in an acidic aqueous reaction environment, and in the presence of an effective amount of an agent for increasing the rate of arsine gas production; and the arsine gas is reacted with an indicator for arsine gas. Beneficially, in accordance with the invention, a rate-increasing metal cation is used as the agent.

The inventive method is useful for analysis of an aqueous sample, which may be an extract. In accordance with the invention, a soil sample may advantageously be subjected to a digestion reaction in the presence of an oxidizing agent, to obtain an aqueous extract for the arsenic reduction reaction. Other extracts may, of course, be prepared, and thereafter analyzed as described herein.

In addition, the inventive method is useful for analysis of arsenic level in humans. Thus, in accordance with the inventive method, a urine sample may be analyzed for arsenic. Advantageously in this and other applications of the invention, a pad carrying the indicator, may be covered with a removable, gas permeable protective layer.

Beneficially, in accordance with one aspect of the invention, Fe(II) or Fe(III) is used as the rate-increasing agent. In a highly preferred embodiment, a mixture of iron and nickel cations is used. In this embodiment, substantially complete arsenic reduction may be effected within about 10 minutes.

Other rate-increasing metal cations may be advantageously used in the inventive method. Beneficially, these other metal cations are divalent metal cations or are metal cations of greater valency than divalent.

When a sample may include an interfering oxidizable substance such as hydrogen sulfide, the inventive method advantageously may further include prior to the arsenic reduction reaction, an oxidation reaction to produce, for instance, non-interfering sulfate ion. In accordance with the inventive method when the oxidation reaction is used, the sample may be adjusted prior to the oxidation reaction, to an acidic pH, and iron cation may beneficially be present during the oxidation reaction. Alternatively, the oxidation reaction may be carried out without prior adjustment of the sample pH, and iron cation may beneficially be present during the oxidation reaction; or, if desired, the sample pH may be adjusted to an alkaline pH.

Advantageously, in accordance with another beneficial aspect of the inventive method when the oxidation reaction is used, the arsenic reduction reaction may be carried out without the intervening step of adding EDTA salts described in, the Hach analysis. As can be understood, both time and money may be saved.

In accordance with yet another aspect of the inventive method, an acidifying agent in powder, granule or other non-liquid form is used to acidify the reaction environment. Preferably, the acidifying agent may be a non-corrosive type acidifying agent such as L-tartaric acid.

Additional advantages and beneficial features of the present invention are set forth in the detailed description, and in part will become apparent to those skilled in the art upon examination of the detailed description or may be learned by practice of the invention.

DETAILED DESCRIPTION OF THE INVENTION

In accordance with the present invention, it has been discovered that in an acidic aqueous reaction environment the rate of arsine gas production is increased by the use of certain metal cations, and that as a result, a relatively greater percentage of arsenic is reduced to arsine gas within a comparable time period. For example, investigation indicates that within the thirty minute time period allowed for the arsenic reduction reaction in the foregoing commercially available analyses, substantially less than 50%, possibly only 25% or even less, of arsine gas is detected.

Based on these and other discoveries, the present invention is directed to an improved method for the analysis of arsenic, that beneficially can provide a higher percentage of arsine gas production in a comparable or significantly shorter (for example, ten minutes) time period. Furthermore, because of relatively increased arsine gas production, the inventive method can provide increased sensitivity for low levels of arsenic. Thus, this method is useful for low levels of arsenic in the range of 2 or 3 ppb to about 5 or 7 ppb or more, up to about 10 ppb, as well as for higher levels of arsenic up to 50 or 100 ppb or more, even in excess of 500 ppb. Moreover, in a preferred aspect, the inventive method relies upon a non-corrosive type acidifying agent. Also in accordance with the inventive method., the arsenic reduction reaction may be controlled whereby, for instance, undesired splashing of the reaction mixture is reduced. In addition, the inventive method can provide greater reproducibility of results.

In accordance with the present invention, an aqueous sample is used for the analysis. The aqueous sample may be an extract. In accordance with the invention, an aqueous extract of soil may beneficially be prepared by adding arsenic-free water and an oxidizing agent, and digesting the mixture by lightly boiling the mixture for a suitable period of time, typically, about one hour. A useful oxidizing agent is Oxone®. Oxone® is a trademark and product of duPont, and includes potassium peroxymonosulfate and potassium peroxydisulfate as oxidizing agents. It will, of course, be understood that any other suitable oxidizing agent for the digestion step, may be used in place of Oxone®. A suitable amount of the oxidizing agent in the case of Oxone®, is about 0.65 g for a 1 g soil sample. In accordance with the invention, the digestion may be carried out without adjustment of the sample to an alkaline pH. Furthermore, as described relative to an optional oxidation step useful in the inventive method, iron cation may beneficially be present during the digestion to minimize interference with removal of hydrogen sulfide interference.

Although the sample volume for analysis can vary, a beneficial volume will typically be in the range of 50 to 300 ml, for example, 50, 100 or 250 ml. If a low level of arsenic is suspected, it may be beneficial for a relatively larger volume to be used, for example, 250 ml instead of 100 ml. In the case of an aqueous sample of small volume, the sample may be diluted to the desired analysis volume, provided that the dilution factor is taken into account.

A suitable temperature of the aqueous sample will range between about 20° to 40° C., preferably about 25° to 30° C. A lower or higher temperature can be expected to respectively slow or increase the rate of arsenic reduction. Although a lower or higher temperature may be corrected for (for example, at 15° C., a 50% longer reaction time), it is generally recommended that the temperature of the sample be within the suitable temperature range. Accordingly, when heat is used to prepare an extract, the extract should be allowed to cool.

In accordance with the present invention, arsenic is reduced to arsine gas in an acidic aqueous reaction environment. Typically, the method will include adjustment of the aqueous sample to an appropriate acidic pH, in which case an acidifying agent may be used for the pH adjustment.

Useful acidifying agents available in powder, granule or other particulate form include corrosive type acidifying agents such as sulfamic acid, and non-corrosive type acidifying agents such as organic acids including L-tartaric acid, succinic acid and citric acid. Useful acidifying agents in liquid form include mineral acids. Mineral acids include phosphoric acid, sulfuric acid and hydrochloric acid, for instance, 85 wt. % phosphoric acid, 18N sulfuric acid and 6N hydrochloric acid.

By the term "corrosive type acidifying agent" as used herein, is meant an acidifying agent that causes visible destruction of, or irreversible alterations in, living tissue by chemical action at the site of contact. Thus, an acidifying agent is a corrosive type acidifying agent if, when tested on the intact skin of albino rabbits by the method currently described by the U.S. Department of Transportation in Appendix A to 49 CFR part 173, it destroys or changes irreversibly the structure of the tissue at the site of contact following an exposure period of four hours. In the description of the subject inventive method, this type of acidifying agent is differentiated from "non-corrosive type acidifying agents", which are available in particulate form.

It has been found that useful acidifying agents affect the rate of arsine gas production in varying degrees, but that an increase in the amount of a particular acidifying agent typically produces an increase in the rate of arsine gas production. Taking into account convenience and safety, in accordance with one aspect of the inventive method, useful acidifying agents available in particulate form are generally preferred over useful acidifying agents in liquid form. Furthermore, when selecting a useful acidifying agent available in particulate form, a non-corrosive type may be advantageously chosen.

Beneficially, the hereinafter-described rate-increasing metal cations allow use of a relatively safer, easier to handle acidifying agent, and even use of a relatively small amount thereof, and yet provide significant benefits and advantages. For instance, although there may be a relatively higher reactivity of rate-increasing metal cations when used with sulfamic acid. or a mineral acid compared to a non-corrosive type acidifying agent such as L-tartaric acid, the relatively higher reactivity may result in undesired splashing on the test strip during the arsenic reduction reaction. Thus, better control of the reduction reaction may be achieved by the selection of a relatively safer, easier to handle acidifying agent.

For optimization purposes, the pH of the acidic reaction environment for the arsenic reduction reaction is beneficially 2.1 or less. A pH significantly above 2.1 (for instance, 2.5) may result in a reduced rate of arsine gas production. A pH in the range of 0.9 to 2.1 will generally be achievable by selecting an appropriate amount of a useful acidifying agent available in particulate form. A pH in the range of 0.15 to 0.9 or more will generally be achievable by selecting an appropriate amount of a useful mineral acid; however, a pH less than 0.3 or 0.4 will typically not be desirable because of the type acidifying agent and amount of acidifying agent needed. When a particular pH is targeted, a sufficient amount of an appropriate acidifying agent is added to the sample to attain the desired pH. Salts of acids including sodium citrate and other salts of organic acids may be used in combination with an acidifying agent to adjust pH.

In a preferred embodiment of the inventive method, the reduction of arsenic to arsine gas is based upon using zinc as a reducing agent. It will, of course, be understood that any other suitable reducing agent-for reducing arsenic in an acidic aqueous environment to arsine gas, may be used in place of zinc, provided that use as hereinafter described, of a rate-increasing metal cation increases the rate of arsine gas production. The reducing agent is conveniently used as a powder or in other particulate form, and generally a relatively finer powder is preferred. For a brief period of time (generally 15 seconds or less) immediately following the addition of the reducing agent, it will be typically beneficial to promote mixing of the resulting mixture.

In the case of zinc, zinc dust of less than 10 microns (or 325 mesh) may be particularly beneficial with a relatively weaker acidifying agent such as a non-corrosive type acidifying agent. A useful amount of zinc for a 100 ml sample volume is typically about 1.8 g, and for a 250 ml sample volume is typically about 3.6 g.

When the inventive method includes adjusting the aqueous sample to an appropriate acidic pH, it may be beneficial for the pH adjustment to precede the addition of the reducing agent. In this way, the pH can be confirmed and any further suitable pH adjustment carried out prior to beginning the generation of arsine gas. However, as in the case of the previously described Merck analysis, the reducing agent may be added prior to the pH adjustment. Benefit also may be found with this reverse order of addition.

In accordance with the present invention, arsenic in an aqueous sample is reduced to arsine gas in an acidic reaction environment and in the presence of an effective amount of agent for increasing the rate of arsine gas production, as hereinafter described. Initially, it was surprisingly discovered in trying to mask iron interference by the addition of ferrous sulfate when arsenic is reduced to arsine gas in an acidic reaction environment, that ferrous sulfate increases the rate of gas production. Thereafter, it was determined that the rate of production of arsine gas is increased, and was found that certain other metal cations may be used as a rate-increasing agent. These cations include divalent metal cations and metal cations of greater valency than divalent. Accordingly, a group VIII (as defined by the CAS version of the Periodic Table) cation such as Fe, Co and Ni, Sn cation, and Cu cation may be used as a rate-increasing metal cation, particularly in accordance with an aspect of the invention in which an acidifying agent in particulate form, in particular a non-corrosive type acidifying agent, is used. Less benefit, if any in some instances, has been found for $Sn^{2+}$ as a rate-increasing agent when a mineral acid is used as an acidifying agent, whereas particular benefit has been found in combination with tartaric acid.

Typically, a salt of a useful metal cation such as $Fe^{2+}$, $Fe^{3+}$, $Co^{2+}$, $Ni^{2+}$, $Sn^{2+}$ and $Cu^{2+}$, and an anion from which an acid may be derived, such as a sulfate, chloride, oxalate and acetate anion, will be used. Thus, exemplary rate-increasing agents are iron(II)sulfate.$7H_2O$, iron(II) chloride.$4H_2O$, iron(II)oxalate, iron(III)sulfate hydrate, cobalt (II)acetate.$4H_2O$, nickel (II)acetate, nickel(II) sulfate.$6H_2O$, tin(II)chloride.$2H_2O$, copper(II)acetate.$H_2O$, and mixtures thereof such as a mixture of iron and nickel salts, for example, a mixture of iron(II)sulfate.$7H_2O$ and nickel(II)sulfate.$6H_2O$. In certain cases such as when iron (II)chloride, iron(III)sulfate, or cobalt(II)acetate is used with tartaric acid, or iron(II) oxalate is used, the aqueous reaction mixture may take on color upon the addition of the rate-increasing agent, but there does not appear to be any interference with the analysis.

As indicated, a benefit of iron cation as a rate-increasing agent is that iron cation may be used to mask iron interference. Furthermore, an iron salt such as ferrous sulfate is inexpensive and safe to handle. Moreover, as later described, it has been discovered that iron cation has a further benefit when the inventive method includes an oxidation reaction prior to the arsenic reduction reaction. Also, in accordance with a highly preferred embodiment of the invention, it has been found that a mixture of iron and nickel salts is an especially preferred rate-increasing agent, in that substantially complete arsenic reduction may be effected within about 10 minutes.

Although the mechanism by which the rate-increasing agent functions remains unclear, both hydrogen gas and arsine gas are typically produced during the arsenic reduction reaction of the inventive method. In any event, it is clear that an effective amount of a useful metal cation increases the rate of arsine gas production, and that the rate of arsine gas production is enhanced as the concentration of the metal cation is increased. However, other considerations may limit the useful concentration of the metal cation. For example, at or above a certain concentration, the rate of gas formation can result in splashing of the reaction mixture on the indicator pad, or the rate of formation of arsine gas can be too rapid for other reasons. Also, at or above a certain concentration, there can be interference between a useful metal cation and other useful agents such as an oxidizing agent. Furthermore, in the case of a metal cation such as $Cu^{2+}$, too high a concentration may have a rate-suppressing effect.

An advantageous concentration of a useful metal cation for the arsenic reduction reaction, is typically about 80 to 100 ppm. However, use of a higher concentration may be appropriate depending upon the metal cation, the result desired, and any concentration-limiting consideration. When an oxidizing agent is used in the presence of iron cation, interference with the oxidizing agent may result in the case of a concentration of iron cation substantially in excess of 100 ppm. Although as explained, the rate of arsine gas production is enhanced as the concentration of the metal cation is increased, sufficient benefit will, generally speaking, be obtained using a small amount up to about 400 ppm of a rate-increasing metal cation, such that a concentration in excess of about 1200 ppm will typically not be used in the arsenic reduction reaction. When a mixture of metal cations is used, for instance a mixture of two metal cations such as an iron salt and a nickel salt, it is typically advantageous for a 10 minute reaction, for each metal cation to be used at a level of about 40 to 50 ppm.

As indicated, in accordance with the inventive method, the concentration to be used of a particular metal cation, will also vary depending upon the extent to which it is desired to enhance the rate of production of arsine gas. Thus, when a particular time end point for the arsenic reduction reaction is targeted, a sufficient amount of the metal cation selected is used to attain sufficient arsine gas production within the time period. This amount of the metal cation will vary such that less of a relatively more effective cation is necessary, whereas more of a relatively less effective cation will be needed. Likewise, the minimum effective concentration varies depending upon the particular metal cation selected and the acidifying agent used.

By reference to the TABLE and accompanying Examples, a skilled artisan can understand the relative reactivity of exemplary rate-increasing metal cations depending upon the acidifying agent selected. From the TABLE, it may be understood that $Ni^{2+}$ salts and certain iron salts can be especially effective rate-increasing agents. In addition, a $Ni^{2+}$ salt in combination with an iron salt is especially effective as a rate-increasing agent.

When the method includes adjusting the aqueous sample to an appropriate acidic pH, the rate-increasing agent may be added with the acidifying agent, but will not be added before the acidifying agent if reduced color development may result. This difference further illustrates the complexity of the chemistry.

When the aqueous sample may include an interfering oxidizable substance such as hydrogen sulfide, the inventive method beneficially may further include prior to reducing arsenic to arsine gas, an oxidation reaction. For this purpose, a suitable oxidizing agent is Oxone®, a known oxidizer of hydrogen sulfide to non-interfering sulfate ion. Other reduced sulfur compounds including mercaptans, other sulfides, disulfides and sulfites, may also be oxidized to non-interfering sulfate ion. It will, of course, be understood that any other suitable oxidizing agent for removing sulfide interference, may be used in place of Oxone®. Advantages of Oxone® include its availability as a dry powder, and that prior to use, it is a relatively stable oxidizer.

When an oxidation reaction is used, a sufficient amount of the oxidizing agent is beneficially added to the aqueous sample to remove interfering sulfide. Conveniently, enough oxidizing agent, for example, 0.65 g of Oxone®, is added to remove up to 3 mg/L hydrogen sulfide, but in such case, a level of sulfide exceeding 3 mg/L hydrogen sulfide, can be expected to interfere with the analysis. In addition, a skilled artisan will appreciate that if the rate-increasing metal ion is to be present during the oxidation reaction but may have an interfering effect, relatively more oxidizing agent should be used. A suitable reaction time for the oxidation step will typically range from about 15 seconds, often 1 minute or less, to 5 minutes.

Prior to adding the oxidizing agent, the aqueous sample may be acidic, for instance pH of 2.1 or less, approximately neutral, or alkaline, for instance pH of about 9. Prior to the oxidation reaction, the aqueous sample may be adjusted to an appropriate acidic pH for the arsenic reduction reaction, provided that consideration is given to any interference of the resulting acidic environment with the oxidation reaction. In accordance with the inventive method, iron cation may be advantageously added prior to the oxidation reaction to minimize any such interference. An effective level of iron cation for this purpose will depend upon factors including the level of interfering sulfide in the sample, the amount of the oxidizing agent, and the extent to which interference is to be minimized. Thus, for example, a relatively higher concentration of interfering sulfide, or elimination of interference may require a relatively higher level of iron cation. A useful level of iron cation may thus range from about 20 or 40 ppm up to about 100 ppm or more, but will typically not be substantially in excess of 100 ppm. It may therefore be understood that the use of iron cation in the inventive method can be doubly advantageous, both benefitting an oxidation reaction, and subsequently the arsenic reduction reaction.

Alternatively, when the oxidation reaction is used, the oxidation reaction may be carried out without prior adjustment of the sample pH. In such case and when Oxone® is used as the oxidizing agent, the addition of Oxone® to the sample may result in an acidic sample pH. Accordingly, in accordance with the inventive method, iron cation may be advantageously added prior to the oxidation reaction in an amount effective to minimize interference with the oxidation reaction, and in this regard, reference is made to earlier description of useful levels of iron cation.

Also to be considered in selecting an order of addition is that certain rate-increasing metal cations may interfere with the oxidation reaction. For example, when the aqueous sample has been adjusted to an appropriate acidic pH, and $Ni^{2+}$, $Co^{2+}$, or $Sn^{2+}$ has also been added to the aqueous sample, the $Ni^{2+}$, $Co^{2+}$, or $Sn^{2+}$ may interfere with the oxidation reaction. Here again, in accordance with the inventive method, iron cation may be advantageously added to the sample prior to the oxidation reaction in an amount effective to minimize any such interference, and in this regard, reference is again made to earlier description of useful levels of iron cation. It may therefore be understood that in a case where prior to the oxidation reaction a mixture of $Ni^{2+}$ and iron cation has been added to the sample, and where the sample has been acidified either prior to the oxidation reaction or in the course of effecting the oxidation reaction, iron cation can have multiple advantages: benefitting the oxidation reaction by eliminating any interference of an acidic reaction environment with the oxidation reaction, benefitting the oxidation reaction by eliminating any interference of the $Ni^{2+}$ with the oxidation reaction, and benefitting the arsenic reduction reaction. To avoid any interference with the oxidation reaction by a rate-increasing agent that may interfere with the oxidation reaction, it may be desirable to add such a rate-increasing agent, after the oxidation reaction.

Also to be considered is that, as mentioned, the oxidizing agent may interfere with activity of the metal cation. Thus, $Cu^{2+}$ may be rendered inactive or may be significantly reduced in effectiveness as a rate-increasing agent by Oxone®. In such case, neutralization of the oxidizing environment prior to adding $Cu^{2+}$ may be a beneficial choice. However, in accordance with another beneficial aspect of the inventive method, except in the case of a metal cation such as $Cu^{2+}$, it is not necessary to neutralize the oxidizing environment prior to adding the metal cation. In any event, the additional steps required by the Hach analysis may be omitted.

To obtain an alkaline pH of about 9 prior to adding the oxidizing reagent, it will generally be necessary to adjust the sample to the target alkaline pH. A disadvantage with such an approach, is that it will be necessary to thereafter readjust the pH to an acidic pH for the arsenic reduction reaction. By comparison, if the oxidation step is carried out without adjusting the sample to an alkaline pH, an additional pH adjustment step is advantageously avoided, thereby reducing the time required for analysis, and avoiding the additional costs of an agent for the alkaline pH adjustment, and of the extra acidifying agent needed to neutralize the alkalinity. Thus, there is benefit in carrying out the oxidation reaction without adjusting the sample to an alkaline pH in preparation for the oxidation reaction.

Beneficially in the case of a urine sample or if otherwise useful, a defoamer may be added prior to the arsenic reduction reaction. For this purpose, an effective amount of a conventional defoamer may be used. A suitable defoamer may be prepared by diluting 1 ml Kelmar Industries antifoam #S-670WS with 9 ml of distilled water. When an oxidation reaction is to be carried out prior to the arsenic reduction reaction, the defoamer will typically be added after the oxidation reaction. A useful amount of the defoamer, which may be, for example, 1 or 2 drops, will vary depending upon the type sample and the particular defoaming agent selected. In any event, dissipation of foam is beneficially allowed to occur prior to the arsenic reduction reaction.

Advantageously, the arsenic to arsine gas reduction reaction may be carried out in a closed reaction bottle of appropriate volume to provide a headspace above the aqueous reaction mixture, and the bottle cap is used to hold a test strip carrying a suitable indicator for arsine gas, in the headspace. Conveniently, the bottle cap may include a slit opening and the indicator may be carried by a pad on the test strip, in which case the pad is disposed in the headspace for reaction of the indicator with arsine gas, and a portion of the remainder of the test strip may extend outside the reaction bottle through the cap slit. Beneficially, the pad is sufficiently spaced away from the aqueous mixture to avoid contact by the aqueous mixture.

In accordance with an advantageous embodiment of the invention, the test strip including the indicator pad, may be covered with a gas permeable protective layer, to prevent any splatter on the pad during the arsenic reduction reaction. This feature of the invention beneficially allows a relatively more reactive reaction environment for the arsenic reduction reaction. Thus, an acidifying agent that affects the rate of arsine gas production more than a typical non-corrosive type acidifying agent, may be used, or may be used in combination with a relatively more reactive rate-increasing metal cation or mixture of rate-increasing metal cations, to provide sufficient reactivity for the type sample being analyzed, for instance a urine sample, or alternatively for example, to reduce the time needed for the arsenic reduction reaction. A gas permeable medium such as commercially available, gas permeable filter paper, may be used as the protective layer. The protective layer should be removably attached to allow for color matching of the indicator pad after removal of the protective layer. Conventional adhesive may be used for attachment of the protective layer. However, generally speaking, it is preferred that the acidifying agent, the rate-increasing metal cation, the amount of the acidifying agent, and the amount of the metal cation be chosen so that the arsenic reduction reaction is sufficiently controlled to prevent any splatter on the indicator pad.

A suitable indicator for arsine gas is mercuric bromide. It will, of course, be understood that any other suitable indicator for arsine gas, may be used. Conveniently, the test strip or pad may be impregnated or saturated with the indicator using conventional techniques. Useful test strips are known in the prior art.

As previously explained, in accordance with the present invention, it has been found that because the arsine gas production rate is increased by the use of rate-increasing metal cations in an acidic reaction environments a higher percentage of inorganic arsenic, in particular $As^{3+}$ and $As^{5+}$, is converted to arsine gas, within a like time period, compared to the foregoing commercially available arsenic tests. Thus, by the present invention, in excess of 50%, typically about 60 to 70% or more, of arsenic reduction occurs within about 30 minutes. Furthermore, comparable results are obtainable in a significantly shorter time period, typically in the range of about 5 to 20 minutes, and in a highly preferred embodiment as exemplified by Example 8, which follows, substantially complete reduction occurs within about 10 minutes. The time allowed for the arsenic reduction reaction will typically be in the range of several minutes to 30 minutes, but may be about 5, 10, 15 or 30 minutes, with consideration given to the time appropriate for maximum color development from the arsenic reduction reaction.

Because of relatively increased arsine gas production, sensitivity may be enhanced particularly for low levels of arsenic in the range of 2 or 3 ppb to about 5 or 7 ppb or more, up to about 10 ppb. The inventive test is also beneficial for higher levels of arsenic up to 50 or 100 ppb or more, even in excess of 500 ppb or more. After the first 15 seconds or less after the reducing agent is added, there is typically no need, unlike certain of the foregoing analyses, to swirl the reaction mixture; rather, the reaction mixture may be allowed to stand undisturbed.

After the allowed time for the arsenic reduction reaction has passed, the indicator color is conveniently visually evaluated, typically by comparison with an appropriate standardized color chart. Generally, it will be best to carry out the color comparison within about 30 seconds after the indicator has been removed from the reaction environment, because after about 30 seconds, the indicator color may begin to change. Also, it will typically be best to avoid direct sunlight when color matching. When the test strip or pad is covered with a gas permeable protective layer, the protective layer should be removed prior to color matching.

In connection with Examples 1–24, sufficient NIST arsenic standard is added to arsenic-free tap water or distilled water, to give an aqueous solution having a concentration of 50 ppb arsenic. Solutions having a temperature of 20 to 28° C., are analyzed. The solutions are free of hydrogen sulfide. In these and the other examples and throughout this description, all parts and percentages are weight percent unless otherwise specified.

EXAMPLE 1

100 ml of an aqueous solution containing 50 ppb arsenic, is added to a 160 ml reaction bottle.

Thereafter, a powder containing 3.5 g of L-tartaric acid and iron(II)sulfate.$7H_2O$ (80 ppm $Fe^{+2}$), is added to the aqueous sample, and the mixture is shaken vigorously for 15 seconds. The resulting solution has a pH of 1.5. Thereafter, 0.65 g of Oxone® powder is added, and the mixture is shaken vigorously for 15 seconds, and then allowed to stand undisturbed for 2 minutes. Thereafter, 1.8 g of zinc powder is added and the mixture is shaken vigorously for 15 seconds, after which the reaction bottle is closed with a bottle cap that has a slit opening and holds a test strip pad carrying mercuric bromide indicator in the headspace above the aqueous reaction mixture.

After 30 minutes in an undisturbed, well-ventilated area, the test strip is removed and within the next 30 seconds, the pad color is visually compared with a

TABLE

| Ex | Acid | Rate-Increasing Agent,ppm | Result (ppb) |
| --- | --- | --- | --- |
| 1 | L-tartaric | $Fe(SO_4).7H_2O$, 80 | 50 |
| 2 | L-tartaric | NONE, 0 | 10 |
| 3 | L-tartaric | Ni(II)acetate, 80 | 50 |
| 4 | L-tartaric | $FeCl_2.4H_2O$, 80 | 50+ |
| 5 | L-tartaric | $Ni(SO_4).6H_2O$, 80 | 75 |
| 6 | L-tartaric | Fe(II)oxalate, 80 | 75 |
| 7 | L-tartaric | $Fe_2(SO_4)_3.XH_2O$, 159 | 75 |
| 8 | L-tartaric | $Fe(SO_4).7H_2O$, 46 $Ni(SO_4).6H_2O$, 44 | 50 |
| 9 | L-tartaric | $SnCl_2.2H_2O$, 80 | 50 |
| 10 | L-tartaric | Co(II)acetate.$4H_2O$, 80 | 50+ |
| 11 | succinic | NONE, 0 | 5 |
| 12 | succinic | $Fe(SO_4).7H_2O$, 80 | 50 |
| 13 | citric | NONE, 0 | 10 |
| 14 | citric | $Fe(SO_4).7H_2O$, 80 | 75 |
| 15 | citric | Ni(II)acetate, 80 | 50 |
| 16 | sulfamic | NONE, 0 | 5 |
| 17 | sulfamic | $Fe(SO_4).7H_2O$, 80 | 50 |
| 18 | sulfamic | Ni(II)acetate, 80 | 150 |
| 19 | sulfamic | $FeCl_2.4H_2O$, 80 | 50 |
| 20 | sulfamic | Co(II)acetate.$4H_2O$, 80 | 100 |
| 21 | sulfamic | $Ni(SO_4).6H_2O$, 80 | 100 |
| 22 | sulfamic | Fe(II)oxalate, 80 | 75 |
| 23 | HCl | NONE, 0 | 15 |
| 24 | HCl | $Fe(SO_4).7H_2O$, 80 | 50 | printed color chart standardized at different levels of arsenic (0, 0.005, 0.010, 0.02, 0.05, 0.1, 0.2, 0.3, 0.5, >0.8 ppm)

using 3.5 g of L-tartaric acid, iron(II)sulfate.7H$_2$O (80 ppm Fe$^{+2}$), 1.8 g zinc powder, and the arsenic reduction reaction procedure just described. The result for this Example is set forth in the TABLE.

EXAMPLES 2–24

Following the procedure of Example 1, further analyses are carried out, using 3.5 g of the acids, the rate-increasing agents, and ppm of the cations of the agents specified in the TABLE. Variations from the procedure include the following: in Example 8, a reaction time of 10 minutes, instead of 30 minutes, is used for the arsenic reduction reaction; and in Exs. 23 and 24, 10 ml of 6N acid is used. The comparable pH is 2.0 in Example 12, 1.7 in Example 14, 1.0 in Example 17, and 0.6 in Ex. 24. The results are set forth in the TABLE.

A relatively greater ppb result for a like period of time for the arsenic reduction reaction, indicates relatively more reduction to arsine gas, and hence a relatively greater rate-increasing effect. Furthermore, a result in excess of 50 ppb indicates relatively more reduction to arsine gas than is provided using 3.5 g L-tartaric acid and iron(II)sulfate.7H$_2$O (80 ppm Fe$^{+2}$), used as explained to prepare the standardized color chart.

In the case of Example 8, in which the reaction time for the arsenic reduction reaction is 10 minutes, rather than 30 minutes, the observed bubbling is found to be very active for the first five minutes and then to gradually taper off during the next five minutes, and it appears that by the end of 10 minutes, reduction of arsenic to arsine gas is substantially complete. By comparison, in the case of a 100 ppb arsenic standard using the reaction system of Example 1 and a thirty minute reaction time, reduction to arsine gas is found to be relatively greatest during the 5$^{th}$ through 20$^{th}$ minutes, in particular during minutes 10 through 15.

EXAMPLE 25

Again following the procedure of Example 1 except that the oxidation step is omitted, L-tartaric acid (3.5 g) is used with Cu(II)acetate.H$_2$O (80 ppm$^{+2}$). A result of 50 ppb is found.

By comparison, if the oxidation step is carried out, a result of 10 ppb is obtained. Because 10 ppb is the same result as that obtained for Example 2, in which tartaric acid is used without a rate-increasing additive, it appears that the oxidation step interferes with a rate-increasing effect f Or Cu$^{+2}$.

EXAMPLE 26

A soil sample having a concentration of 4 mg/Kg arsenic, is prepared using NIST arsenic standard. The soil sample (1 g) is added to a reaction vessel containing 10 ml of arsenic-free, hydrogen sulfide-free water. 0.65 g of Oxone® powder is added and the mixture is digested by being lightly boiled for one hour. Thereafter, the mixture is allowed to cool to room temperature, and the entire contents of the reaction vessel are added to a 160 ml reaction bottle, and water free of arsenic and hydrogen sulfide is used to bring the volume of the contents to 100 ml. Thereafter, a powder containing 3.5 g of L-tartaric acid and iron(II)sulfate.7H$_2$O (80 ppm Fe$^{+2}$) is added to the sample, and the mixture is shaken vigorously for 15 seconds.

Thereafter, 1.8 g of zinc powder is added and the remaining procedure of Example 1 is followed; however, the arsenic concentration is determined from a specifically calibrated color chart. The color chart shows a value of 0.05 mg/L, and this value is multiplied by a dilution factor of 100 (1 g sample diluted to 100 ml) to obtain an arsenic concentration of 5 mg/L (or 5 mg/Kg) in the soil sample.

EXAMPLE 27

A urine sample having a spiked concentration of 100 ppb arsenic, is prepared using NIST arsenic standard. 5 ml of the urine sample is added to a 160 ml reaction bottle, and water free of arsenic and hydrogen sulfide is used to bring the volume to 100 ml. Thereafter, a powder containing 3.5 g of sulfamic acid, nickel(II)sulfate.6H$_2$O (44 ppm Ni$^{+2}$), and iron(II)sulfate.7H$_2$O (46 ppm. Fe$^{+2}$), is added to the sample, and the mixture is shaken vigorously for 15 seconds. Thereafter, 0.65 g of Oxone® powder is added, and the mixture is shaken vigorously for 15 seconds, and then allowed to stand undisturbed for 2 minutes. Thereafter, 1 drop of defoamer prepared by diluting 1 ml Kelmar Industries antifoam #S-670WS with 9 ml of distilled water, is added, the mixture is shaken for 2 seconds, and the foam is allowed to dissipate.

Thereafter, 1.8 g of zinc powder is added and shaken vigorously for 5 seconds, after which the reaction bottle is closed with a bottle cap that has a slit opening and holds a test strip pad carrying mercuric bromide indicator in the headspace above the aqueous reaction mixture. The test strip has a gas permeable filter paper over the test pad to prevent any splatter on the test pad during the arsenic reduction reaction.

After 20 minutes in an undisturbed, well-ventilated area, the test strip is removed from the cap, the protective gas permeable filter paper is taken off, and within the next 30 seconds, the pad color is visually compared with a standardized color chart specifically prepared for urine analysis. An arsenic concentration of 100 ppb is found in the urine sample.

EXAMPLE 28

Following the procedure of the foregoing commercially available Hach Arsenic Test Kit (Cat. No. 27999-00), 50 ml of a hydrogen sulfide-free aqueous sample having a concentration of 50 ppb NIST arsenic standard is added to the Hach test kit reaction bottle. Thereafter, Reagent #1 (sodium phosphate, dibasic) of the test kit is added to the sample and the resulting mixture is swirled to dissolve the powder. As a result, the sample is adjusted to a pH of 9.4. Thereafter, Reagent #2 (Oxone®) is added and the resulting mixture is swirled to dissolve the powder, after which 3 minutes is allowed for the oxidation reaction. Thereafter, to neutralize the oxidizing environment, Reagent #3 (EDTA disodium salt, EDTA tetrasodium salt) is added and the resulting mixture is swirled to mix, and after 2 minutes the resulting mixture is again swirled to mix. Thereafter, Ni(II)acetate (80 ppm Ni$^{+2}$) is added when 1 scoop of Reagent #4 (sulfamic acid) is added, and the resulting mixture is swirled to mix. Thereafter, Reagent #5 (zinc powder) is added and the resulting mixture is swirled to mix, and the reaction bottle is closed using the Hach test kit black cap with Hach test strip inserted. The arsenic reduction reaction is allowed to occur for 30 minutes, during which time the mixture is swirled twice. Thereafter, the test strip is removed from the bottle cap and immediately compared with the Hach color chart. The result approximately corresponds to 300 ppb, thereby indicating that approximately six times as much of the arsenic is converted to arsine gas by using a rate-increasing agent in accordance with the present invention.

The present invention may be carried out with various modifications without departing from the spirit or essential attributes thereof, and accordingly, reference should be made to the appended claims, rather than to the foregoing specification as indicating the scope of the invention.

What is claimed is:

1. A method for arsenic analysis comprising reducing inorganic arsenic to arsine gas with a reduction agent in an acidic aqueous reaction environment and in the presence of an effective amount of an agent for increasing the rate of the arsine gas production, wherein the rate-increasing agent comprises Fe(II) or Fe(III); and analytically detecting the arsine gas.

2. The method of claim 1, further comprising subjecting a soil sample to a digestion reaction in the presence of an oxidizing agent under conditions sufficient to obtain an aqueous extract of the soil for the arsenic reduction reaction.

3. The method of claim 1, further comprising prior to the arsenic reduction reaction, carrying out an oxidation reaction to reduce interference with the arsenic analysis.

4. The method of claim 3, wherein said oxidation reaction is carried out in an acidic environment and in the presence of an effective amount of Fe(II) cation to benefit said oxidation reaction.

5. The method of claim 1, wherein said rate-increasing agent further comprises Ni(II).

6. The method of claim 1, wherein an acidifying agent in particulate form is used to acidify the reaction environment for the arsenic reduction reaction.

7. The method of claim 1, wherein the analytical detection comprises reacting the arsine gas with an indicator for arsine gas, and the indicator is covered by a gas permeable protective layer during the arsenic reduction reaction.

8. A method for arsenic analysis comprising reducing inorganic arsenic to arsine gas with a reduction agent in an acidic aqueous reaction environment and in the presence of an effective amount up to about 1200 ppm of an agent for increasing the rate of the arsine gas production, wherein an acidifying agent in particulate form is used to acidify the reaction environment, and wherein at least one metal cation is used as the rate-increasing agent, and said at least one metal cation is divalent or of greater valency than divalent; and analytically detecting the arsine gas.

9. The method of claim 8, wherein said acidifying agent is a non-corrosive type acidifying agent.

10. The method of claim 8, wherein said at least one metal cation is selected from the group consisting of Fe, Co, Ni, Cu and Sn cations, and mixtures thereof.

11. The method of claim 8, wherein said rate-increasing agent comprises Fe(II) or Fe(III) as said at least one metal cation.

12. The method of claim 11, wherein said rate-increasing agent further comprises Ni(II).

13. The method of claim 8, further comprising subjecting a soil sample to a digestion reaction in the presence of an oxidizing agent under conditions sufficient to obtain an aqueous extract of the soil for the arsenic reduction reaction.

14. The method of claim 8, further comprising prior to the arsenic reduction reaction, carrying out an oxidation reaction to reduce interference with the arsenic analysis.

15. The method of claim 14, wherein said oxidation reaction is carried out in an acidic environment and in the presence of an effective amount of Fe(II) cation to benefit said oxidation reaction, and wherein said rate-increasing agent comprises said Fe cation.

16. A method for arsenic analysis comprising subjecting an aqueous sample to an oxidation reaction to reduce interference with the arsenic analysis, wherein said oxidation reaction is carried out in an acidic environment and in the presence of an effective amount of Fe(II) cation to reduce any undesirable effect of said B2 acidic environment on said oxidation reaction; and thereafter reducing inorganic arsenic in said aqueous sample to arsine gas with a reducing agent and analytically detecting the arsine gas.

17. The method of claim 16, wherein said oxidation reaction is carried out without prior adjustment of the pH of said sample.

18. The method of claim 16, wherein prior to said oxidation reaction, an acidifying agent in particulate form is used to acidify said sample, and ferrous sulfate provides said Fe(II).

19. The method of claim 16, wherein the arsenic reduction reaction is carried out in the presence of an effective amount of an agent for increasing the rate of the arsine gas production, and said rate-increasing agent comprises said Fe(II) cation and at least one metal cation selected from the group consisting of Co, Ni and Sn cations.

20. The method of claim 19, wherein said rate-increasing agent is a mixture of Fe(II) and Ni cations.

* * * * *

UNITED STATES PATENT AND TRADEMARK OFFICE
CERTIFICATE OF CORRECTION

| | |
|---|---|
| PATENT NO. | : 6,696,300 B1 |
| APPLICATION NO. | : 10/045387 |
| DATED | : February 24, 2004 |
| INVENTOR(S) | : Ivars Jaunakais, Lea Marianne Jaunakais and Corlyss Brown Lewis |

It is certified that error appears in the above-identified patent and that said Letters Patent is hereby corrected as shown below:

Claim 1, column 13,
Line 6, "reduction" should read "reducing".

Claim 8, column 13,
Line 33, "reduction" should read "reducing".

Claim 16, column 14,
Line 23, delete "B2" after "undesirable effect of said".

Signed and Sealed this
Nineteenth Day of July, 2011

David J. Kappos
*Director of the United States Patent and Trademark Office*